United States Patent [19]

Pacey et al.

[11] Patent Number: 4,734,376

[45] Date of Patent: Mar. 29, 1988

[54] PROCESS FOR THE SPECTROPHOTOMETRIC MEASUREMENT OF LITHIUM ION EMPLOYING A CHROMOGENIC AZA-12-CROWN-4- ETHER

[75] Inventors: Gilbert E. Pacey, Oxford, Ohio; Ken-ichi Sasaki, Nagoya, Japan

[73] Assignee: The President & Trustees of the Miami University, Miami, Fla.

[21] Appl. No.: 921,459

[22] Filed: Oct. 22, 1986

Related U.S. Application Data

[62] Division of Ser. No. 698,019, Feb. 4, 1985, Pat. No. 4,659,815.

[51] Int. Cl.$^4$ .................... G01N 21/75; G01N 33/20; G01N 33/50
[52] U.S. Cl. ........................................ 436/79; 436/74; 436/164; 436/178
[58] Field of Search .................... 436/74, 79, 164, 178

[56] References Cited

U.S. PATENT DOCUMENTS

| | | | |
|---|---|---|---|
| 4,367,072 | 1/1983 | Vogtle et al. | 436/501 |
| 4,436,923 | 3/1984 | Pacey et al. | 436/74 X |
| 4,645,744 | 2/1987 | Charlton et al. | 436/74 |

FOREIGN PATENT DOCUMENTS

| | | | |
|---|---|---|---|
| 0125555 | 11/1984 | European Pat. Off. | 436/74 |
| 8204253 | 12/1982 | Norway | 260/330.6 |

OTHER PUBLICATIONS

Lockhart et al., Journ. Anal. Chem. Society, Perkins Trans I (1973) England "Preparation of Some Nitrogen-Containing Polyether Crown Compounds", pp. 577-581.

G. E. Pacey et al., Talanta (1984), vol. 31, No. 3, "Ion-Pair Extractions with 12-Crown-4 and its Analogues", pp. 165-168.

Nakamura et al., Chemistry Letters, pp. 1305-1306, 1981.

Nakamura et al., Analytical Chemistry, vol. 52, No. 11, pp. 1668-1671, 1980.

*Primary Examiner*—Barry S. Richman
*Assistant Examiner*—Robert J. Hill, Jr.
*Attorney, Agent, or Firm*—Marshall, O'Toole, Gerstein, Murray & Bicknell

[57] ABSTRACT

Chromogenic aza-12-crown-4 ethers which can be used for the spectrophotometric determination of lithium ion in aqueous solutions are disclosed. The compounds of the invention are particularly useful for the analysis of $Li^+$ in the presence of $Na^+$, a situation common in biological and geological systems. The compounds [e.g., 1-(2-oxy-5-nitrobenzyl)-1-hydro-1-aza-4,7,10-trioxacyclododecane], their methods of manufacture, and methods of utilizing the compounds for the analysis of lithium are disclosed.

11 Claims, 5 Drawing Figures

PROCESS FOR THE SPECTROPHOTOMETRIC MEASUREMENT OF LITHIUM ION EMPLOYING A CHROMOGENIC AZA-12-CROWN-4- ETHER

This is a division of application Ser. No. 698,019, filed Feb. 4, 1985, U.S. Pat. No. 4,659,815.

BACKGROUND OF THE INVENTION

The present invention relates to novel chromogenic crown ethers and to the use of the ethers as reagents for the selective extraction and colorimetric determination of lithium. The compounds of the invention have the structural formula:

wherein X and Y are, respectively, (i) OH and $NH^+$; (ii) $O^-$ and N, or (iii) $O^-$ and $NH^+$. When X is OH and Y is $NH^+$, the compound is systematically named, 1-(2-hydroxy-5-nitrobenzyl)1-hydro-1-aza-4,7,10-trioxacyclododecane; when X is $O^+$- and Y is N, 1-(2-oxy-5-nitrobenzyl)-1-aza-4,7,10-trioxacyclododecane; and, when X is $^-$ and Y is $NH^+$, 1-(2-oxy-5-nitrobenzyl)-1-hydro-1-aza-4,7,10-trioxacyclododecane. All three of these compounds are, generically, chromogenic aza-12-crown-4 ethers.

Selective reagents which permit the isolation of a particular ion from a complex matrix or mixture of ions are of interest to those in the chemical or bio-chemical analytical fields. When the matrix in question includes two or more cations of the Group I metals, it is often difficult to selectively isolate one of the Group I cations from the mixture without interference from other cations in the system. With respect to biological systems, such as blood serum, which contains a relatively large amount of sodium ion, a reagent having the ability to selectively (and quantitatively) extract lithium ion in the presence of sodium ion is of interest for bio-chemical assays.

The ability of crown ethers to selectively extract alkali and alkaline earth metal ions has been recognized in the art [Pedersen, C. J., J.Am.Chem.Soc. 1967, 89, 7017]. Nonetheless, there has been little successful work in utilizing these compounds in analytical determinations until quite recently, e.g., U.S. Pat. No. 4,436,923 to Pacey and Bubnis, which describes a crown ether reagent which can be used for the spectrophotometric determination of potassium ion in the presence of sodium ion.

Of particular interest to the background of the present invention is the crown ether N-(2-hydroxy-5-nitrobenzyl)-aza-15-crown-5 which was reported to be a selective extractant for lithium ion. [Nakamura, H., Sakka, H., Takagi, M. and Ueno, K., Chem.Lett., 1981, 1305]. Although this compound exhibited good extraction efficiency for lithium ion ($-\log K)_{LiL}^{ex}=9.15$), the extraction efficiency of the reagent for sodium ion was of the same order of magnitude ($-\log K_{NaL}^{ex}=9.76$). Thus the compound exhibited relatively poor selectivity in that it displayed only slightly more affinity for the lithium ion.

Another compound which is of interest to the chromogenic aza-12-crown-4 compounds of the present invention is the cryptand [2,1,1].

which was reported to extract lithium ions more selectively and more efficiently than the reagent of Nakamura et al. [Wu, Y. and Pacey, G., American Chemical Society 15th Central Regional Meeting, Miami University, Ohio, 1983, No. 18 (May 23–25, 1983)]. However, not only is the Wu et al cryptand difficult to synthesize, but the cryptand also requires an ion pairing agent, resazurin, in order to exhibit sensitivity to lithium. That is, the [2,1,1]cryptand itself is not sensitive to lithium ions.

SUMMARY OF THE PRESENT INVENTION

The present invention provides novel chromogenic crown ethers, viz, (i) 1-(2-hydroxy-5-nitrobenzyl)-1-hydro-1-aza-4,7,10-trioxacyclododecane; (ii) 1-(2-oxy-5-nitrobenzyl)1-aza-4,7,10-trioxacyclododecane; and, (iii) 1-(2-oxy-5-nitrobenzyl)-1-hydro-1-aza-4,7,10-trioxacyclododecane. It has been found that the presence of these structures is pH dependent. If the pH is low (less than 5), structure i will predominate. At higher pH's (greater than 11), compound ii represents the reagent structure. At a pH of approximately 8, a structure such as iii will predominate.

Reagents formed from these aza-12-crown-4 compounds exhibit affinity for lithium ion, and are substantially unreactive to potassium, rubidium, cesium and ammonium ions. Although the aza-12-crown-4 reagents exhibit some sensitivity to sodium, the affinity of the reagents for lithium ion is over two orders of magnitude (100 times) greater than their affinity for sodium ion.

Useful aqueous reagent compositions will result when the concentration of the aza-12-crown-4 ether is in the range $1\times10^{-4}$M to $1\times10^{-2}$M. The $10^{-4}$M concentration approximates the detection limit of the crown ether-lithium compound extracted to organic phase. On the other hand, use of concentrations in excess of $10^{-2}M$ does not result in increased sensitivity with accuracy.

A base is required in the reagent system to ensure optimum properties. Both NaOH and KOH are suitable bases, but potassium hydroxide is generally preferred due to interference effects of the sodium ion on the absorbance during spectrophotometric analysis. The optimum concentration of hydroxide base is approximately $1 \times 10^{-2}M$ to $1 \times 10^{-1}M$, although lower concentrations can be employed with some sacrifice in sensitivity.

The basic, aqueous reagent composition can be added to aqueous samples containing lithium ion resulting in the formation of a lithium ion/crown ether complex. Subsequent extraction of the sample with an organic solvent will cause the lithium ion/crown ether complex to pass into the organic phase. The absorbance of the organic phase can be measured against a reagent blank utilizing conventional spectrophotometric techniques. Although a number of organic solvents can be employed, it has been found that chloroform is preferred. When a reagent composition of the invention was added to aqueous solutions containing $Na^+$ and $Li^+$ in the weight ratio 30:1 and the solution was extracted with organic solvent, absorbance increased 8% when compared to a control containing $Li^+$, alone, notwithstanding the presence of the large excess of sodium ion. Thus, aza-12-crown-4 compounds exhibit a high degree of selectivity for lithium in matrices which contain both lithium ion and sodium ion. The aza-12-crown-4 reagents can be synthesized as follows:

with potassium hydroxide. The procedure utilized is set forth in Example 6.

DETAILED DESCRIPTION

The preparation of the reagent aza-12-crown-4 compounds and their use as a reagent for the determination of lithium ion are illustrated in the following examples:

EXAMPLE 1—Preparation of 3-benzyl-1,5-diol-3-azapentane (1).

Benzyl chloride (158g, 1.25 mol) was stirred in a water-cooled reaction vessel while diethanolamine (126g. 1.2 mol) was gradually added. The temperature of the reaction mixture was kept below 70° C. until it became homogeneous and heat release stopped. The mixture was then kept at 70° C. for more than 1 hour, and, after cooling, dissolved into 200 ml of 1 M hydrochloric acid. The aqueous solution was extracted four

BRIEF DESCRIPTION OF THE DRAWINGS

Figure 1:
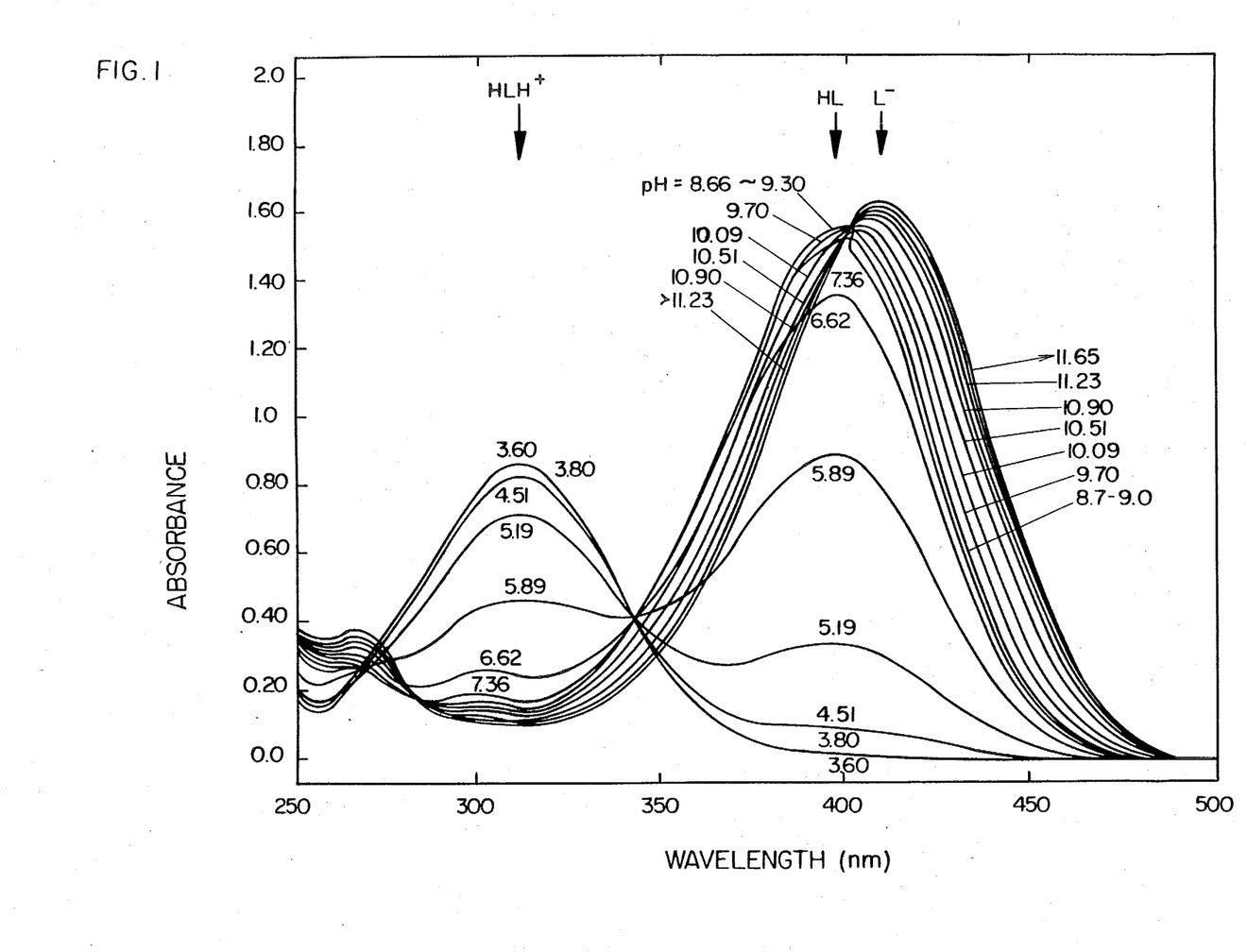

FIG. 1 shows the ultraviolet-visible spectra of an aqueous solution containing a chromogenic aza-12-crown-4 reagent of the present invention, hydrochloric acid and cesium chloride while undergoing titration times with 100 ml chloroform washes. To the aqueous solution, 300 ml of 5 M NaOH was added with water cooling in order to isolate the oily product. The oil layer was mixed with 300 ml of chloroform, washed with 100 ml of water and dried over anhydrous magnesium sulphate. The chloroform solution was evaporated to dryness. The pure compound (1) was obtained as light-yellow oil. Yield 67%; $^1$HNMR (CDCl$_3$): δ 2.50–2.68 (t, 4H, N—CH$_2$), ~3.2 (br, 2H, OH), 3.41–3.60 (t, 4H,O—CH$_2$; s(3.60), 2H, Ar—CH2), 7.10 (s, 5H, Ar—H).

EXAMPLE 2—Preparation of 1,5-dichloro-3-oxapentane (2).

Utilizing a procedure similar to that described in the literature [Pedersen, C.J., *J.Am.Chem.Soc.*, 1967, 89, 7017], diethylene glycol was chlorinated with thionyl chloride in the presence of pyridine in benzene. The product was purified by vacuum distillation (0.7 Torr, 40°–0.25 Torr, 35° C.). Yield 69%; $^1$HNMR (CDCL$_3$): δ3.4–3.9 (m, 8H).

EXAMPLE 3—Preparation of 1-benzyl-1-aza-4,7,10-trioxacyclododecane (3).

The cyclization of the diol(1) prepared in Example 1 with the dichloride(2) prepared in Example 2 was performed under the template effect of Li$^+$ ions in a highly diluted solution in accordance with a procedure suggested in the literature [Miyazaki, T., Yanagida, S., Itoh, A., Okahara, M., *Bull. Chem. Soc. Jpn.*, 1982, 55, 2005]. A 1.6 liter portion of t-butylalcohol was refluxed together with lithium metal (6.2g, 0.9 mol) with stirring for two hours. Diol(1) (58.5 g, 0.3 mol) dissolved in 50 ml of t-butylalcohol was added to the reaction mixture and refluxing was continued for an additional 2 hours. Dichloride (2) (42.9 g, 0.3 mol) and lithium bromide (26 g, 0.3 mol) were added to the reaction vessel and the heterogeneous mixture was refluxed for 10 days to ensure reaction. The alcohol solvent was evaporated by using a rotary evaporator. Water (250 ml) was added to the residue to dissolve the inorganic salts and isolate a reddish-brown oil. The oil layer was mixed with 60 ml of chloroform, washed three times with 1M sodium hydroxide (30 ml), and slowly mixed with 100 ml of 5M hydrochloric acid while maintaining room temperature by water cooling. Thereafter, the aqueous layer was washed three times with chloroform (50 ml) and 80 ml of 4M sodium hydroxide was added slowly to a cooled vessel containing the aqueous solution, to isolate the oil. The cooled mixture was extracted with chloroform, the organic layer was dried over anhydrous magnesium sulphate, and evaporated to dryness under vacuum. The pure compound (3) was obtained by vacuum distillation (0.027 Torr. 112° C. −0.04 Torr, 123° C.). Yield 63%; $^1$HNMR (CDCl$_3$): δ 2.5–2.75 (m, 4H, N—CH$_2$), 3.35–3.65 (m, 14H, O—CH$_2$, Ar—CH$_2$), 7.10(s, 5H, ArH).

EXAMPLE 4—Preparation of 1-aza-4,7,10-trioxacyclododecane (4).

A quantity of the 1-benzyl-1-aza-4,7,10-trioxacyclododecane compound (3) prepared in Example 3 (45.1 g, 0.17 mol), ethanol (7 g), and 10% palladium on carbon (0.5 g) were shaken in hydrogen atmosphere at more than 50 psi (1 psi= 6.9×10$^3$ Pa=0.07 kg cm$^{-2}$). Hydrogen gas was recharged several times into the reaction chamber to keep the pressure elevated. Shaking was continued until the pressure lowering stopped (4 days). After the palladium carbon was filtered, the solvent was evaporated. The pure compound (4) was sublimed from the residue with gentle heating using a water bath (75°–77° C.; crude material melted at this temperature). The sublimate was white needles and was hygroscopic. Yield 60%; $^1$HNMR (D$_2$O): δ 2.53–2.70 (t, 4H, N—CH$_2$), 3.5–3.75 (m, 12H, O—CH$_2$), no signal at 7.1 (Ar—H of benzyl group, possible contaminant).

EXAMPLE 5—Preparation of 1-(2-oxy-5-nitrobenzyl)-1-hydro1-aza-4,7,10-Trioxacyclododecane (5).

The aza-crown 4 prepared in Example 4 (1.05 g, 0.0060 mol), freshly distilled tetrahydrofuran (THF; 50 ml), and potassium hydroxide pellets (0.8 g, 0.014 mol) were placed in a flask. A solution of 2-hydroxy-5-nitrobenzyl bromide (1.40 g, 0.0060 mol) dissolved in THF was added with vigorous stirring, which was continued overnight (14 hr). Examination of the reaction flasks revealed that bright yellow and white powders had been produced, and the potassium hydroxide pellets had been completely consumed. After evaporation of the solvent, the residue was dissolved into water (20 ml), and 6M hydrochloric acid (~45 drops) was added until the solution turned colorless or pale yellow (di- or mono-protonated form respectively). The solution was extracted with chloroform while undergoing drop-wise titration with 5M potassium hydroxide. The effect of the titration was to convert the diprotonated compound to the monoprotonated dipolar ion (5), which was easily extracted to chloroform. The titration and shaking for extraction were continued until no increase in color intensity in the aqueous layer was observed during the titration. The aqueous layer was twice extracted with chloroform (20 cc). All the chloroform solutions were combined, washed with water (20 ml) four times, filtered with dry filter paper, and evaporated to dryness. In order to remove water-insoluble impurities, the residue was dissolved into water, filtered and evaporated to dryness. The pure compound (5) was obtained by the dissolution of the residue into chloroform and evaporating it to dryness in vaco with heating (80°–90° C.). The compound (5) (bright yellow) crystallized slowly from a glassy solid. Yield: 93%; m.p.: 98.5° C. $^1$HNMR (CDCl$_3$): δ 2.6–2.8 (m, 4H, N—CH$_2$), 3.5–3.8 (m, 14H, O—CH$_2$, Ar—CH$_2$), 6.62–6.77 (d, 1H, Ar—H) 7.72–8.02 (m, 2H, Ar—H). Anal. Found: C, 55.30%; H, 7.04%; N, 8.52%. Calcd for C$_{15}$H$_{22}$O$_6$N$_2$: C, 55.19%; H, 6.81%; N, 8.58%.

EXAMPLE 6—Determination of Acid Dissociation Constants, K$_1$ and K$_2$.

A 50 ml aqueous solution containing the crown reagent of Example 5 (8.70×10$^{-5}$M), hydrochloric acid (6×10$^{-4}$M), and cesium chloride (0.1 M) was titrated with potassium hydroxide [0.1 M (below pH12), and 1 M (above pH12)], using a Metrohm automatic titrator, Dosimat E535 equipped with Potentiograph E536. The titration was interrupted in every 0.3–1.5 pH increase for the measurement of the absorption spectrum of the solution. A 3–4 ml portion of the solution was taken to a cuvette, the spectrum was recorded on a Hewlett-Packard 8450A spectrometer, and the solution was returned to the titration vessel using a pipet. The magnitude of the spectrum was corrected in order to adjust for dilution upon titration, and corrected results shown in FIG. 1.

Figure 2:
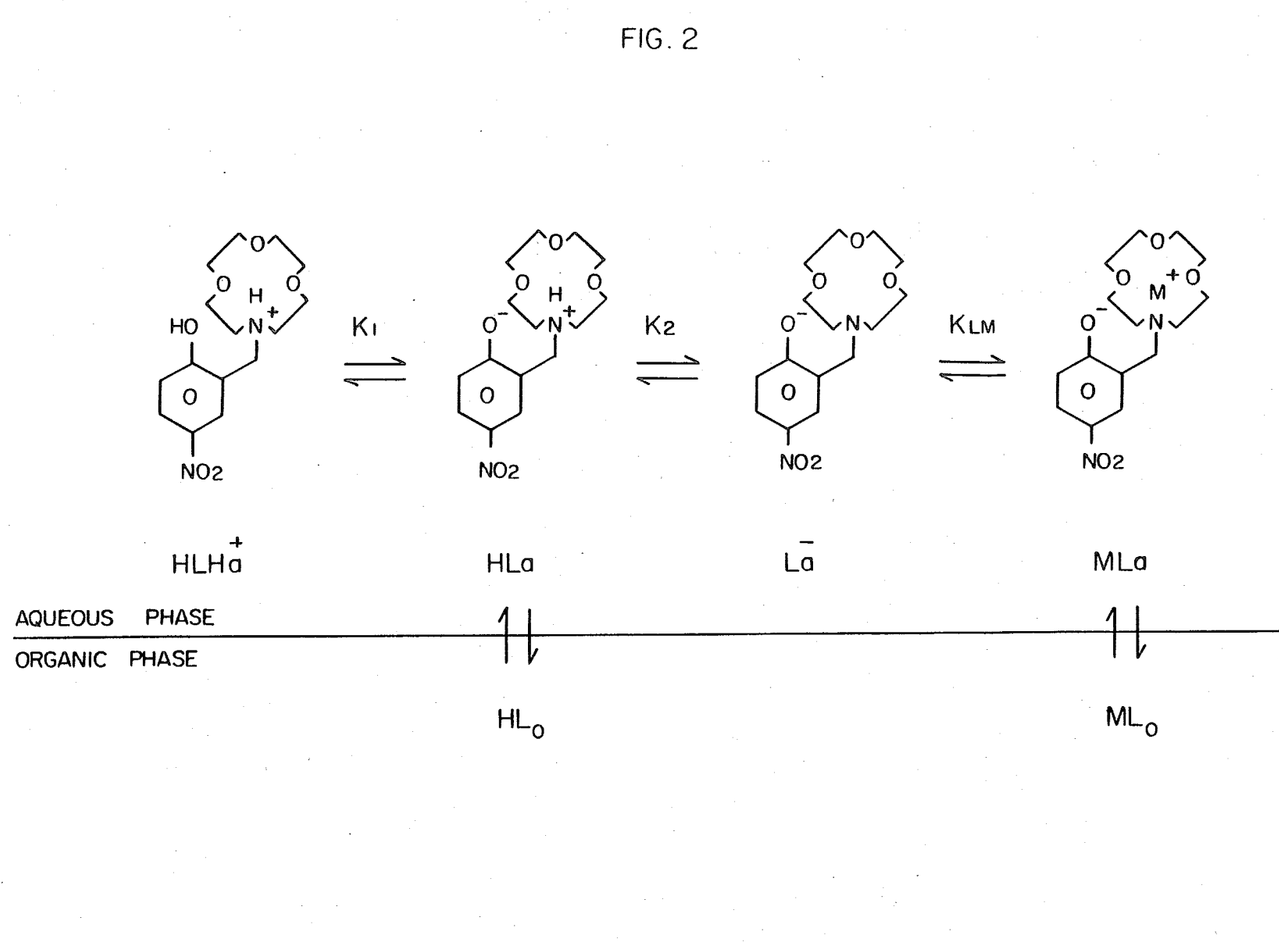
FIG. 2 illustrates the acid dissociation constants $K_1$ and $K_2$ and the complex formation constant $K_{ML}$ for the aza-12-crown-4 reagent of the present invention.

Equilibria for the chromogenic aza-12-crown-4 reagent in an aqueous solution are shown in FIG. 2 and as follows.

$$K_1 = \frac{[HL][H^+]}{[HLH^+]} \quad (1)$$

$$K_2 = \frac{[L^-][H^+]}{[HL]} \qquad (2)$$

$$K_{ML} = \frac{[ML]}{[L^-][M^+]} \qquad (3)$$

value of $-\log K_1$ for the aza-12-crown-4 reagent agrees reasonably with that reported for the aza-15-crown-5 reagent. However, the higher value of $-\log K_2$ for the aza-12-crown-4 compound indicates that the proton of the reagent of the present invention is more tightly bound with the nitrogen atom and that complex formation is enhanced at a pH higher than 10.3.

TABLE 1

| | ACID DISSOCIATION CONSTANTS ($K_1$ and $K_2$) AND EXTRACTION CONSTANT ($K_{ML}^{ex}$) | | | | | |
|---|---|---|---|---|---|---|
| | | | $-\log K_{LiL}^{ex}$ | | $-\log K_{NaL}^{ex}$ | |
| | $-\log K_1$ | $-\log K_2$ | 0.1M KOH | 0.05M KOH | 0.1M KOH | 0.05M KOH |
| aza-12-crown-4 (present invention) | 5.77[a] | 10.31[a] | 10.18[c] | 10.23[c] | 12.50[c] | 12.49[c] |
| aza-15-crown-5 (prior art) | 5.79[b] | 9.69[b] | 9.15[d] | | 9.76[d] | |

[a] $\mu = 0.1$ (CsCl)
[b] $\mu = 0.1$ (CH$_3$)$_4$NCl)
[c] Solvent, chloroform
[d] Solvent, 1,2-dichloroethane; pH, not specified where $K_1$ and $K_2$ denote the acid dissociation constants, and $K_{ML}$ a complex formation constant. By assuming no significant complex-formation, an absorbance A at any wavelength and the total concentration of the reagent $[HL]_t$ are written as $$A = \epsilon_{HLH^+}[HLH^+] + \epsilon_{HL}[HL] + \epsilon_{L^-}[L^-] \qquad (4)$$

$$[HL]_t = [HLH3O] + [HL] + [L^-] \qquad (5)$$

where $\epsilon$'s are molar absorption coefficients. Equations (1) and (2) can be rewritten using Equations (4) and (5) as:

$$-\log K_1 = pH - \log \frac{\epsilon_{HLH^+}[HL]_t - A}{A - \epsilon_{HL}[HL]_t} \qquad (6)$$

$$-\log K_2 = pH - \log \frac{\epsilon_{HL}[HL]_t - A}{A - \epsilon_{L^-}[HL]_t} \qquad (7)$$

assuming $[HL]_t >> [L^-]$ for $K_1$ and $[HL]_t >> [HLH^+]$ for $K_2$. The fact that FIG. 1 exhibits two distinct isosbestic points (342.8 nm and 401.4 nm) depending on pH confirms that $[L^-]$ or $[HLH^+]$ can be neglected as compared with $[HL]_t$ in a certain pH region; thus $[HL]_t >> [L^-]$ at pH $\leq 6.6$ (Eq. (6) is valid), and $[HL]_t >> [HLH^+]$ at pH $\geq 9.7$ (Eq. (7) is valid).

FIG. 1 also shows that, at 401.4 nm and at pH $\leq 6.6$, the absorbance approaching to the isosbestic point reflects the decay of HLH$^+$ and the growth of HL, so that these absorbance data can be used for the evaluation of $-\log K_1$ using Eq. (6). At 342.8 nm and at pH $\geq 9.7$, the absorbance deviating from the isosbestic point reflects the decay of HL and the growth of L$^-$, so that these absorbance data can be used for the evaluation of $-\log K_2$ using Eq. (7).

In Eq. (6) and (7), since [H$^+$] is known experimentally, and since $\epsilon_{HL}[HL]_t$ can be obtained as the average value of absorbances on each isosbestic point, unknown parameters are now only $\epsilon_{HLH^+}[HL]_t$ and $\epsilon_{L^-}[HL]_t$, which can be adjusted to give constant values for $-\log K_1$ and $-\log K_2$, respectively, by applying the observed absorbance sets to the equations.

Figure 3:
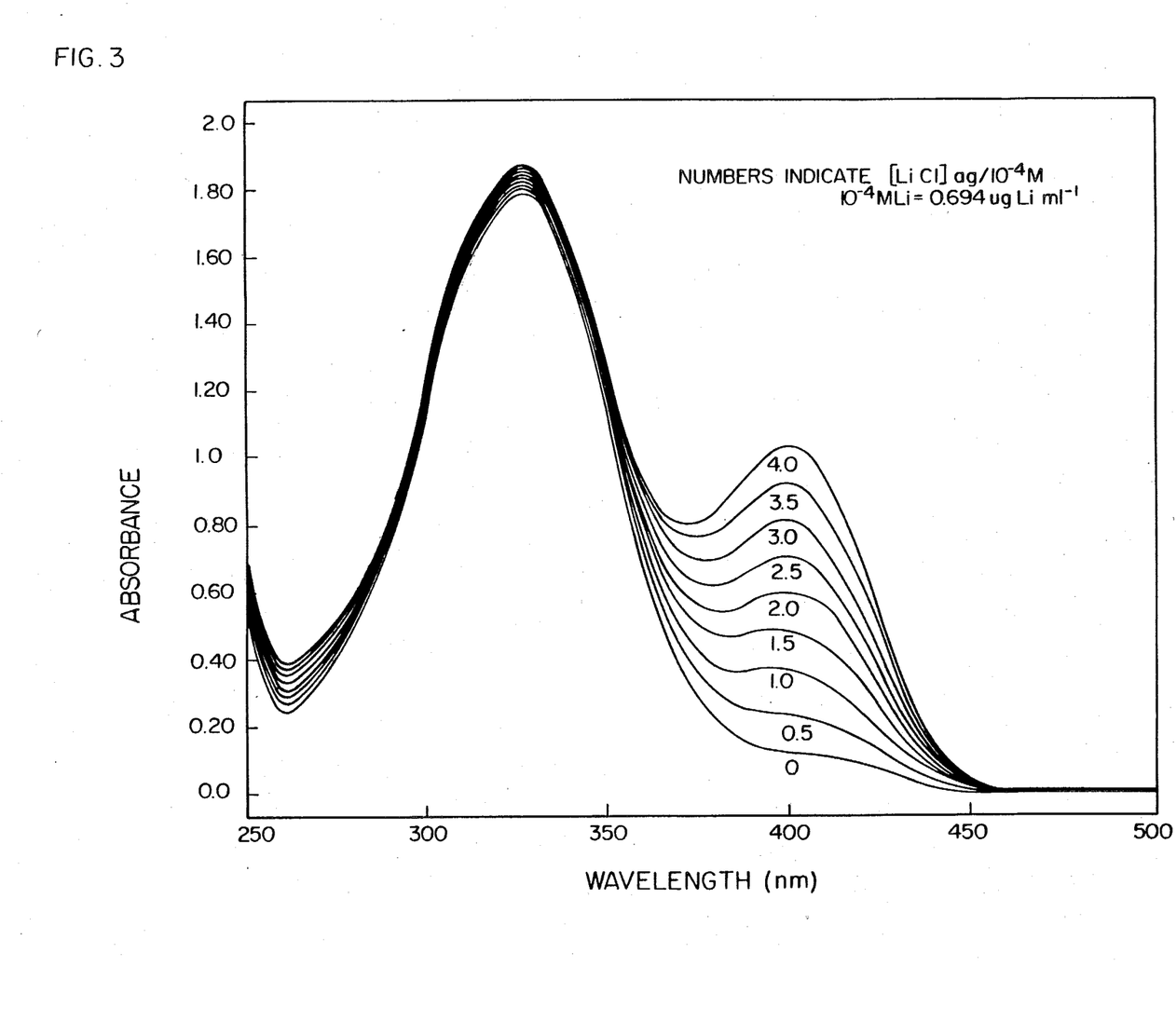
FIG. 3 illustrates the ultraviolet visible spectra of chloroform layers utilized in extracting aqueous basic solutions of lithium chloride and aza-12-crown-4 reagent at nine different levels of lithium ion in accordance with the procedure of Example 7.

Table 1 lists the observed values for $K_1$ and $K_2$ for the chromogenic aza-12-crown-4 reagent of the present invention as well as the reported values for the prior art crown ether, N-(2-hydroxy-5-nitrobenzyl)-aza-15-crown-5 [Nakamura et al, Chem.Lett., 1981, 1305]. The EXAMPLE 7—Solvent extraction of lithium-ion containing solutions Nine 10 ml volumetric flasks were prepared as follows: 1 ml of 1 M KOH and 2 ml of $3.34 \times 10^{-3}$M aza-12-crown-4 reagent were added to each of the flasks; a measured amount of a $10^{-3}$M LiCl solution was added to eight of the flasks in 0.5 ml increments, (i.e., 0.5 ml, 1 ml, 1.5 ml, 2 ml, 2.5 ml, 3 ml, 3.5 ml, 4 ml); thereafter, sufficient water was added to the nine flasks to make the total volume of each flask 10 ml. Five ml aliquots of each of the volumetric flasks were transferred into a series of nine 50 ml round-bottomed flasks, forming aqueous solutions containing a constant amount of both the aza-12-crown-4 reagent ($6.7 \times 10^{-4}$M$=0.22$ μg ml$^{-1}$) and potassium hydroxide ($10^{-1}$M), and a varying amount of lithium chloride -- eight samples ranging from [LiCl]aq$=5 \times 10^{-5}$M through $4 \times 10^{-4}$M (0.35 μg ml$^{-1}$ through 2.8 μg ml$^{-1}$), plus a non-lithium-containing blank. The concentration of hydroxide ion ($1 \times 10^{-1}$M) in each of the samples (including the flask containing no lithium chloride) was chosen based on the previously-determined pK$_2$ value (10.31). Five ml of chloroform was added to each of the round-bottomed flasks, each of the flasks was shaken for 20 minutes and, after shaking, left standing for more than 10 minutes at room temperature (20° ± C. 2° C.). Absorbance of the organic layer was measured at 400 nm using a Hewlett-Packard 8450A UV/VIS spectrophotometer. Spectral data are illustrated in FIG. 3.

A calibration curve was obtained whose linear portion is from 0.3 μg ml$^{-1}$ through 2 μg ml$^{-1}$, which can be expressed as:

$$C_{Li} = 3.00A \pm 0.05$$

where $C_{Li}$ and A denote the concentration of lithium in μg ml$^{-1}$ and the net absorbance (path length: 1 cm) at 400 nm, respectively. The error was calculated from the mean value of the standard devations of triplicate samples over the linear range. The error seemed to be mainly caused by the instability of the absorbance after the separation of the organic layer. The stability was improved, with slight loss of sensitivity and slight increase in interference, by the addition of a small amount of t-butyl alcohol (2% by vol.) to the chloroform, while the blank absorbance increased by a factor of 1.6.

EXAMPLE 8—Determination of extraction constant, $K_{ML}{}^{ex}$.

Extraction equilibria are illustrated in FIG. 2 and in the following equation:

$$K_{ML}^{ex} = \frac{[ML_o][H^+{}_a]}{[HL_o][M^+{}_a]} \quad (8)$$

$$[HL]_t = [HL_o] + [ML_o] + [L^-{}_a] + [HL_a] + [ML_a] \quad (9)$$

$$[M^+] = [M^+{}_a] + [ML_a] + [ML_o] \quad (10)$$

$$E = \frac{A_o}{[HL_o]+[ML_o]} = \frac{\epsilon_{HL_o}[HL_o]+\epsilon_{ML_o}[ML_o]}{[HL_o]+[ML_o]} \quad (11)$$

where $[M^+]_t$ denotes a total alkali metal concentration. By assuming $[L^-{}_a] >> [HL_a]+[ML_a]$, and $[M^+]_t >> [HL]_t$, $$[HL]_t = [HL_o]+[ML_o]+[L^-{}_a] \quad (12)$$

$$[M^+]_t = [M^+{}_a] \quad (13)$$

Combining Eq. (8), (11), (12), and (13) gives $$\frac{1}{E-E^o} = \frac{[H^+{}_a]}{K_{ML}^{ex}\Delta\epsilon} \cdot \frac{1}{[M]_t} + \frac{1}{\Delta\epsilon} \quad (14)$$

and $$E = \frac{A_o}{[HL]_t - (A_a/\epsilon_{La-})} \quad (15)$$

where $\Delta\epsilon = \epsilon ML_o - \epsilon HL_o$, and $E^o$ denotes the E value in the absence of the metal ion in the system ($E^o = \epsilon HL_o$). Eq. (14) shows that the plot of $1/(E^o-E^o)$ against $1/[M]_t$ gives a straight line and that $K_{ML}{}^{ex}$ is calculated from the slope, the intercept, and the pH value. The absorbance at the isosbestic point 401.4 nm shown in FIG. 1 gives $\epsilon_{L-a}$, so that the values of E and $E_o$, which are necessary for the plot, can be obtained experimentally.

Determination of the partition equilibrium system was made in a manner similar to that employed in Example 7. The concentrations $[HL]_t$, $[M^+]_t$, and $[OH^-]$ were $5.35\times10^{-5}$M, $4\times10^{-3}$M-2 M (as chloride), and $10^{-2}$M-$10^{-1}$M (as potassium hydroxide), respectively. Chloroform was used as the organic medium.

In order to confirm the important assumption $[L_a^-] >> [HL_a]+[ML_a]$, Eq.(11) (the left equation) was used for the evaluation of E instead of Eq.(15), which was derived from Eq.(11) under the assumption, and the obtained extraction constants compared with those obtained using Eq.(15). When Eq.(11) was applied, the species $HL_o$ and $ML_o$ in the organic layer were extracted into 0.1M hydrochloric acid as HLH+, and the concentration of HLH+ was determined spectrophotometrically and equated to $[HL_o]+[ML_o]$ in Eq.(11). The extraction constants obtained in this way are $$-\log K_{LiL}^{ex} = 10.25, \text{ and } -\log K_{NaL}^{ex} = 12.47$$

which agreed well with those obtained with the assumption (Table 1).

EXAMPLE 9—Effect of sodium ion

The effect of sodium ion in the system was determined in a procedure similar to that used in Example 7. A series of six round-bottomed flasks containing 5 ml of chloroform, and 5 ml of an aqueous solution containing aza-12-crown-4 reagent ($6.7\times10^{-4}$M), lithium chloride ($1\times10^{-4}=0.694$ μg ml$^{-1}$), and a variable amount of sodium chloride [sodium chloride was added to five of these flasks in 0.001M increments whereby the [NaCl]aq $=1\times10^{-3}$M to $5\times10^{-3}$M (23 μg ml$^{-1}$ through 115 μg ml$^{-1}$); one flask served as a sodium-free blank]. Absorbance of the organic layer was measured on a spectrophotomer. The results are illustrated in FIG. 4.

Figure 4:
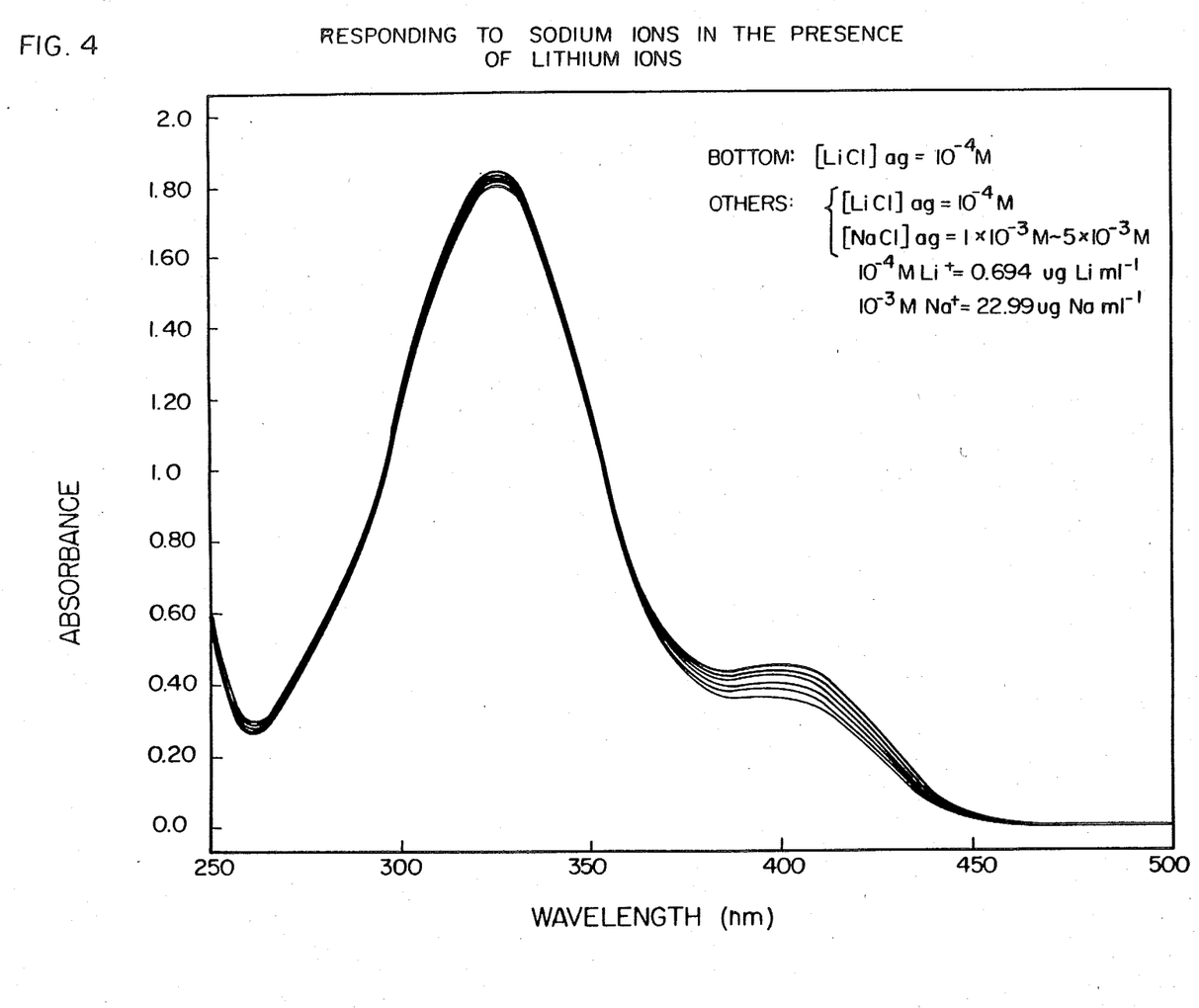
FIG. 4 is the ultraviolet visible spectra of chloroform layers utilized in extracting aqueous basic solutions of lithium ion in the presence of sodium ion and employing a reagent compound of the present invention in accordance with the procedure of Example 9.

An analysis of FIG. 4 at 400 nm reveals that the sodium ion interference was linear in the whole range, and that the presence of a 30-fold excess of sodium ions to lithium ions resulted in only an 8% increase in absorbance.

Figure 5:
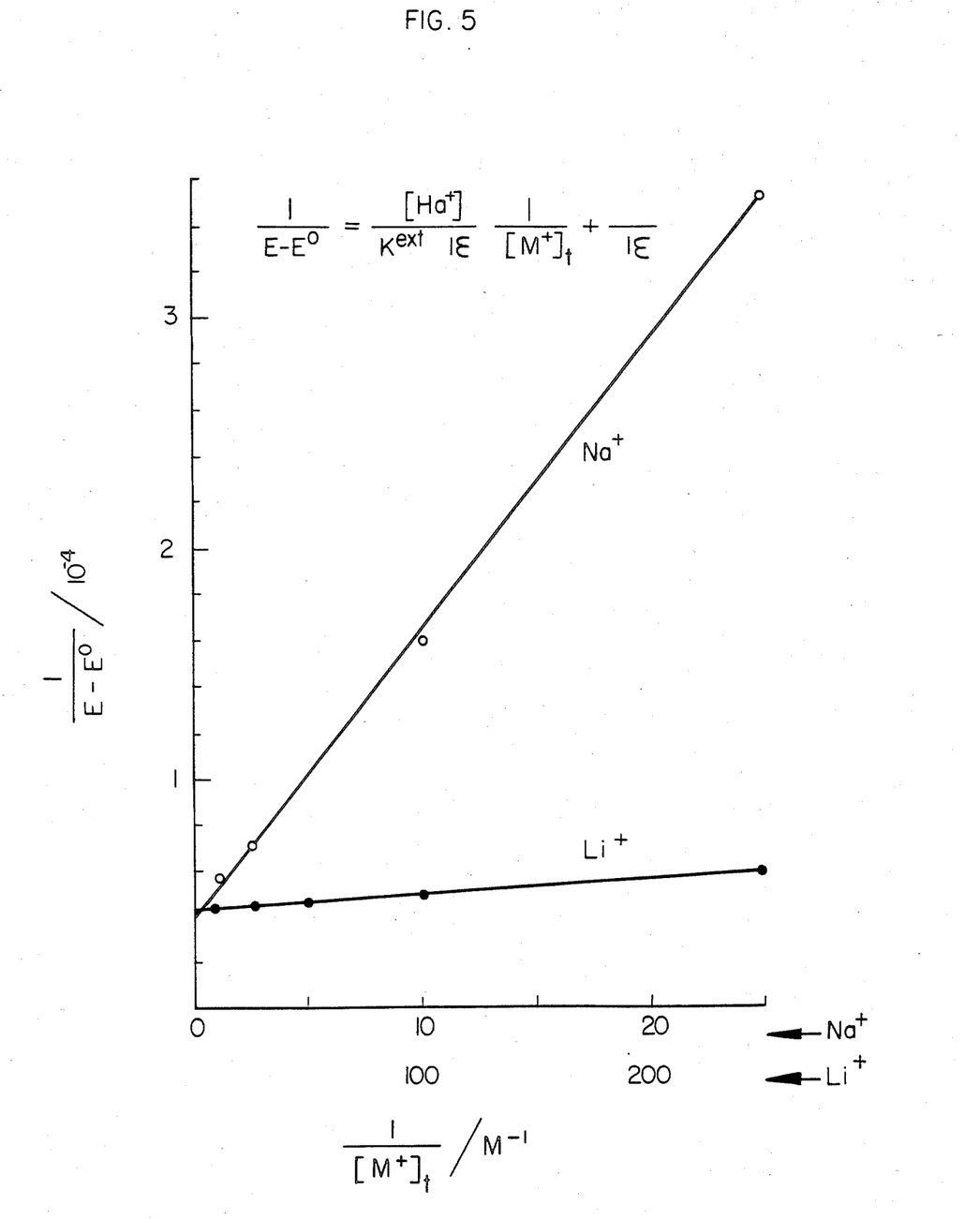
FIG. 5 shows the plots of data obtained for the determination of the extraction constant, $K_{ML}^{ex}$.

FIG. 5 shows the plots of data obtained for the determination of $K_{ML}{}^{ex}$ according to Eq. (14). The plot exhibits good straight lines for the lithium and sodium ion systems, respectively. Table 1 shows the $-\log K_{ML}{}^{ex}$ values obtained from the plots in FIG. 5 and from similar plots, together with that reported for the aza-15-crown-5 compound of the prior art. The $-\log K_{LiL}{}^{ex}$ is not significantly dependent on the hydroxide concentration employed.

When compared with the prior art aza-15-crown-5 compound, the value of $K_{LiL}{}^{ex}$ for the aza-12-crown-4 reagent is smaller by a factor of ten. However, the ratio of $K_{LiL}{}^{ex}$ to $K_{NaL}{}^{ex}$ for the crown-4 is much greater than the aza-15-crown5. Thus, the extraction efficiency of aza-12-crown-4 might be lower than that of aza-15-crown-5, but its selectivity for lithium ions in the presence of sodium ions is much higher.

EXAMPLE 10—Effect of organic solvents and bases

Three solvents—chloroform, 1,2-dichloroethane and methylene chloride—were compared using potassium hydroxide and sodium hydroxide as bases. At 0.01 M hydroxide, no significant sensitivity and interference differences were observed between either the cations of the bases or between the organic solvents. At 0.1M hydroxide, however, large differences were observed both between the cations and between the organic solvents. Potassium hydroxide gave higher sensitivity in both chloroform and methylene chloride than sodium hydroxide, but not in 1,2-dichloroethane. Methylene chloride exhibited the highest sensitivity when used with potassium hydroxide, but was subject to increased interference by sodium ions. The combination of methylene chloride and sodium hydroxide allowed most of the reagent to pass into the organic layer and, as a result, the absorbance could not be measured. The results show that the optimum combination of high sensitivity, low interference, and low blank absorption was achieved by a system employing 0.1M potassium hydroxide and chloroform. The best stability of the absorbance after the separation of organic layer from the equilibrium system was also observed for this system.

Various other organic solvents were tested as organic media with a 0.01 M potassium hydroxide. Nitromethane and 10% nitromethane in chloroform extracted most of the reagent species into the organic phase, so that no response of the reagent to lithium and sodium ion was observed. Methylisobutyl-ketone showed only slight extraction of the metal complex. No extraction occurred into benzene, carbon tetrachloride, chlorobenzene, and trichlorethylene when these solvents were employed.

Although triethylamine (1M in CHCl$_3$) was examined as an organic base, the response to lithium ions was smaller and the response to sodium ions was larger than the preferred KOH inorganic base. A combination of the amine (1M in CHCl$_3$) and sodium hydroxide (0.1M) as base gave an intermediate response to lithium ions, and the response was not stable.

Example 11—Determination of lithium ion content in blood and urine samples.

Samples of human blood serum and urine were analyzed for lithium ion content utilizing a chromogenic aza-12-crown4 ether reagent. The procedure employed was essentially the same for both the blood serum and urine specimens except that larger dilutions were employed with the urine samples due to the higher concentration of lithium ion in urine. Because proteins react with the reagent to form emulsions, the blood serum and urine samples were heat-denatured prior to analysis.

Three specimens of blood serum and four specimens of urine, all of whose lithium ion content had been previously determined, were analyzed utilizing 1-(2-oxy-5-nitrobenzyl)1-hydro-1-aza-4,7,10 trioxacyclododecane reagent. Triplicate 3.0 ml samples of blood serum (nine samples) were transferred to labeled centrifuge tubes and 3 ml of water added to each sample. A similar procedure was followed with respect to the urine specimens, except that 1.0 ml samples were employed and each of the twelve urine samples was diluted with 11 ml of water. The samples were mixed, heated in a boiling water bath for 15 minutes, and centrifuged for 10 minutes. A 2.0 ml aliquot of each of the twenty-one sample solutions was transferred to a series of stoppered centrifuge tubes, and 2.0 ml of the crown ether solution (b 1×10$^{-3}$M), 1 ml of KOH solution (1M) and 5 ml of water was added thereto (total volume=10 ml). Each of the samples was thoroughly mixed to ensure homogeneity, 10 ml of chloroform added to each tube, and the samples were shaken for 10 minutes. After phase separation, the absorbance of the organic phase of each of the samples was measured at 400 nm against a reagent blank. The results are set forth in Table 2.

TABLE 2

| Determination of Lithium ion in Blood Serum or Urine Using Chromogenic Aza-12-Crown-4. | | | |
|---|---|---|---|
| Blood Serum* | | Urine* | |
| Known | Found | Known | Found |
| 3.5 | 3.4 | 10.5 | 10.4 |
| 7.0 | 6.8 | 14.0 | 14.0 |
| 10.5 | 10.3 | 21.0 | 20.8 |
|  |  | 42.0 | 40.7 |

*Triplicate Determination. Results are reported as parts per million.

What is claimed is:

1. A process for the spectrophotometric determination of the concentration of lithium ions in an aqueous solution, said process comprising the following steps:
   (a) mixing in a common vessel:
      (i) a measured quantity of a lithium-ion-containing aqueous soluion; and
      (ii) a measured quantity of the crown ether compound (b) combining said aqueous solution with a measured quantity of a hydroxide containing base;
   (c) adding a measured amount of a water-immiscible organic solvent to said vessel whereby an aqueous phase and an organic phase are formed;
   (d) agitating said vessel to extract any material soluble in said organic solvent into said organic phase;
   (e) transferring a measured quantity of said organic phase into a first spectrophotometric cell and a quantity of a reagent blank into a second spectrophotometric cell;
   (f) scanning said cells with ultraviolet-visible light and recording the relative light absorbance of said organic phase with respect to said reagent blank at a wavelength of approximately 400 nm; and
   (g) determining the concentration of lithium ions in said aqueous solution by comparing said relative absorbance with the relative absorbance at the same wavelength or organic phases obtained by treating aqueous solutions containing known concentrations of lithium ions in accordance with steps a through f.

2. The process of claim 1 wherein said organic solvent is selected from the group consisting of methylene chloride, chloroform and 1, 2-dichloroethane.

3. The process of claim 1 wherein the amount of said organic solvent added to said vessel is substantially equal in volume to the aqueous solution in said vessel.

4. The process of claim 1 wherein said base is selected from the group consisting of potassium hydroxide and sodium hydroxide.

5. The process of claim 1 wherein said scanning step comprises:
   (i) providing a light source which is capable of emitting radiation covering the wavelength range of 250 nm through approximately 500 nm;
   (ii) beaming radiation from said light source through said spectrophotometric cells while varying the wavelength thereof throughout the range 250 nm to approximately 500 nm; and
   (iii) recording the absorbance of said radiation of said organic phase and said reagent blank throughout said wavelength range.

6. The process of claim 1 wherein said organic solvent is chloroform.

7. The process of claim 6 wherein the chloroform includes an amount of t-butyl alcohol improve the stability of the absorbance of the organic phase.

8. A process for the spectrophotometric determination of the concentration of lithium ions in an aqueous solution, said process comprising the following steps:
   (a) mixing in a common vessel:
      (i) a measured quantity of a lithium-ion-containing aqueous soltuion; and
      (ii) a measured quantity of the crown ether compound (b) combining said aqueous soltuion with a measured quantity of a base selected from the group consisting of sodium hydroxide and potassium hydroxide;

(c) adding a measured amount of chloroform to said vessel whereby an aqueous phase and an organic phase are formed;

(d) agitating said vessel to extract any material soluble in chloroform into said organic phase;

(e) transferring a measured quantity of said organic phase into a first spectrophotometric cell and a quantity of a reagent blank into a second spectrophotometric cell;

(f) scanning said cells with ultraviolet-visible light and recording the relative light absorbance of said organic phase with respect to said reagent blank at a wavelength of approximately 400 nm; and (g) determining the concentration of lithium ions in said aqueous solution by comparing said relative absorbance with the relative absorbance at the same wavelength of solutions containing known concentrations of lithium ions which have been treated in accordance with steps a through f.

9. The process of claim 8 wherein said chloroform includes an amount of t-butyl alcohol sufficient to improve the stability of the absorbance of the organic phase.

10. The process of claim 8 wherein the amount of chloroform added to said vessel is substantially equal in volume to the aqueous solution in said vessel.

11. The process of claim 8 wherein said scanning step comprises:

(i) providing a light source which is capable of emitting radiation covering the wavelength range of 250 nm through approximately 500 nm;

(ii) beaming radiation from said light source through said spectrophotometric cells while varying the wavelength thereof throughout the range of 250 nm to approximately 500 nm; and (iii) recording the absorbance of said radiation by said organic phase and said reagent blank through said wavelength range.

* * * * *